(12) United States Patent
Hacket et al.

(10) Patent No.: US 7,709,447 B2
(45) Date of Patent: May 4, 2010

(54) USE OF SPINOSYNS FOR WOUND HEALING

(75) Inventors: Kristina Clare Hacket, North Sydney (AU); Lionel Barry Lowe, Dural (AU)

(73) Assignee: Eli Lilly and Company, Indianapolis, IN (US)

( * ) Notice: Subject to any disclaimer, the term of this patent is extended or adjusted under 35 U.S.C. 154(b) by 243 days.

(21) Appl. No.: 11/568,130

(22) PCT Filed: Apr. 29, 2004

(86) PCT No.: PCT/US2004/011268

§ 371 (c)(1),
(2), (4) Date: Oct. 20, 2006

(87) PCT Pub. No.: WO2005/112950

PCT Pub. Date: Dec. 1, 2005

(65) Prior Publication Data

US 2007/0167379 A1    Jul. 19, 2007

(51) Int. Cl.
*A61K 31/7048* (2006.01)
*C07H 17/08* (2006.01)

(52) U.S. Cl. .......................................... 514/28; 536/7.1
(58) Field of Classification Search .................. 514/28; 536/7.1
See application file for complete search history.

(56) References Cited

U.S. PATENT DOCUMENTS

2003/0026848 A1 * 2/2003 Joshi ........................ 424/600

FOREIGN PATENT DOCUMENTS

| EP | 1 252 820 A | 10/2002 |
| WO | WO 01/11961 A | 2/2001 |
| WO | WO 01/11963 A | 2/2001 |

OTHER PUBLICATIONS

Definition of insect bite, The Free Online Medical Dictionary, http://medical-dictionary.thefreedictionary.com/insect+bite, accessed online on Jun. 22, 2009.*
Definition of wound healing, The Free Online Medical Dictionary, http://medical-dictionary.thefreedictionary.com/Wound+healing, accessed online on Jun. 29, 2009.*
Da, D.H., et al., "Dermal absorption and metabolism of spinosad in lactating goats," *CROPU*, Jan. 1, 1999, XP002153532 abstract.
Kirst, Herbert A., et al., "Evaluation and development of spinosyns to control ectoparasites on cattle and sheep," *Current Topics in Medicinal Chemistry*, 2(7):675-699 (Hilversum, Netherlands).
Letter dated Apr. 30, 2003, informing of a License of a Product for Veterinary Use; License No. 8,593, dated Apr. 29, 2003, Ministry of Agriculture of Federated Republic of Brazil (Original in Portuguese and English translation).

* cited by examiner

*Primary Examiner*—Shaojia Anna Jiang
*Assistant Examiner*—Jonathan S Lau
(74) *Attorney, Agent, or Firm*—James J. Sales; John C. Demeter

(57) ABSTRACT

A spinosyn or a physiologically acceptable derivative or salt thereof for promoting or accelerating wound healing in humans.

14 Claims, No Drawings

USE OF SPINOSYNS FOR WOUND HEALING

The present invention is directed toward the therapeutic use of spinosyns in humans to promote or accelerate would healing in both normal and healing impaired humans. Spinosyns or a physiologically acceptable derivative or salt thereof can be employed for therapeutic indications in humans requiring soft-tissue growth and regeneration. Impaired wound healing is a significant source of morbidity in humans and may result in complications such as non-healing wounds. In the normal individual, wound healing is achieved through an uncomplicated endogenous process. In contrast, impaired wound healing is associated with several conditions such as diabetes, infection, immunosuppression, obesity and malnutrition.

BACKGROUND OF THE INVENTION

Wound healing is a complex biological process involving extracellular matrix, blood cells, parenchymal cells, and mediators such as cytokines. After the wound reaches hemostasis, the point where bleeding stops, the healing process begins. It occurs in three stages: inflammation, tissue formation (proliferation), and tissue regeneration (remodeling). Healing begins very quickly after injury occurs; for example, re-epithelialization of cutaneous wounds begins within hours (Singer and Clark, *New Eng. J. Med.* 341(10): 738-746 (1999)). The process of wound healing is initiated by myelinated afferent sensory nerves which in turn mediate neurogenic inflammation, immunological responses (Eglezos et al., *Adv. Exp. Biol. Med.* 273: 499-503 (1989); *Immunol. Cell Biol.* 69: 285-294 (1991)) and vascular tone (Khalil & Helme, *Brain Res.* 500: 256-262 (1989); *Brain Res.* 527: 292-298 (1990)), which are all essential components of healing. After the initiation of healing by sensory nerves, the process of healing is regulated by growth factors and cytokines that affect cell migration, proliferation, and protein production. In hemostasis, proteins such as fibrin and fibronectin interact to clot the blood, and cytokines and growth factors are upregulated. After injury, inflammation begins.

Inflammatory responses occur in three distinct phases, each apparently mediated by different mechanisms: (1) an acute transient phase, characterized by local vasodilatation and increased capillary permeability; (2) a delayed, subacute phase, most prominently characterized by infiltration of leukocytes and phagocyte cells; and (3) a chronic proliferative phase, in which tissue degeneration and fibrosis occur. Many different mechanisms are involved in the inflammatory process. The ability to mount an inflammatory response is essential for survival in the face of environmental pathogens and injury, although in some situations and diseases the inflammatory response may be exaggerated and sustained for no apparent beneficial reason. During inflammation, neutrophilis (polymorphonuclear leukocytes, PMNs), monocytes and macrophages infiltrate the wound. These phagocytic cells release growth factors for the proliferative phase, enzymatic mediators (proteases) that degrade proteins, and phagocytose bacteria, dead and dying cells thus debriding the wound.

In the next phase, proliferation begins. Collagen is deposited, forming scar tissue. Fibroblasts produce proteoglycans, which bind the collagen fibers together. Over time, the collagen is degraded by proteases and remodeled into a stronger scar structure.

Spinosyns (also known as A83453 factors) are agricultural, livestock and companion animal pesticides that have shown activity against 1) insects in the order Lepidoptera, 2) members of the order Homoptera, 3) members of the insect order Diptera, 4) members of the order Coleoptera, and 5) members of the order Anoplura. Formulations suitable for agricultural, livestock and companion animal administration include various suspensions, solutions, tablets, capsules, liquids and treats.

Spinosad (a product comprised primarily of spinosyn A, 85%, and spinosyn D, 15%) is currently approved in Australia and New Zealand for the treatment of lice on sheep and the treatment and prevention of blowfly strike on sheep. In Brazil, spinosad is approved for the topical treatment and control of certain ticks, flies and lice and as an antiseptic and cicatrizing repellent for treatment of botfly myiasis and skin wounds in cattle, sheep, goats, horses, pigs, birds and dogs.

Spinosyns are known to be useful for controlling lice infestations in a human, U.S. Pat. No. 6,063,771 and EP 1 252 820. Formulations suitable for such pediculicidal use in humans are also described in those patents.

Despite what is known regarding the ectoparasiticidal activity of the spinosyns and the commercial approvals, it has now been discovered that a spinosyn or a physiologically acceptable derivative or salt thereof has wound healing activity independently from a formulation containing an antiseptic/disinfectant agent.

BRIEF SUMMARY OF THE INVENTION

The present invention concerns methods for treating wounds in humans to promote or accelerate wound healing including poor healing or chronic wounds, skin diseases and allergic diseases, particularly those disorders associated with the skin, and conditions or symptoms related thereto, by administering a spinosyn or a physiologically acceptable derivative or salt thereof to a human in need thereof. Preferably, these methods are practiced by administering spinosad or a physiologically acceptable derivative or salt thereof.

DETAILED DESCRIPTION OF THE INVENTION

This invention provides methods for promoting or accelerating wound healing in a human comprising administering a spinosyn or a physiologically acceptable derivative or salt thereof, to a human in need thereof. In another aspect this invention provides the use of a spinosyn, or a physiologically acceptable derivative or salt thereof, or a formulation containing either a spinosyn or derivative or salt thereof, for the manufacture of a medicament for promoting or accelerating wound healing in a human.

Spinosyns are naturally derived fermentation products. They are macrolides produced by cultivation of *Saccharopolyspora spinosa*. The fermentation produces several factors, including spinosyn A and spinosyn D (also called A83543A and A83543D). Spinosyn A and spinosyn D are the two spinosyns that are most active as insecticides. An agricultural product comprised mainly of these two spinosyns (approximately 85% A and 15% D) is available commercially from Dow AgroSciences under the name spinosad. An ectoparasite product comprising spinosad is available commercially from Eli Lilly and Company. The name "spinosad" comes from a contraction of the spinosyns "A" and "D."

Each spinosyn has a 12-membered macrocyclic ring that is part of a tetracyclic ring system to which two different sugars are attached, the amino-sugar forosamine and the neutral sugar 2N,3N,4N-tri-O-methylrhamnose. This unique structure sets the spinosyns apart from other macrocyclic compounds.

Spinosyn A (A83543A) was the first spinosyn isolated and identified from the fermentation broth of *Saccharapolyspora spinosa*. Subsequent examination of the fermentation broth revealed that the parent strain of *S. spinosa* produced a number of spinosyns that have been labeled A to J (A83543A to J). Compared to spinosyn A, spinosyns B-J are characterized by differences in the substitution patterns on the amino group of the forosamine, at selected sites on the tetracyclic ring system and on 2N,3N,4N-tri-O-methylrhamnose. The strains of *S. spinosa* currently in use produce a mixture of spinosyns of which the primary components are spinosyn A (~85%) and spinosyn D (~15%). Additional spinosyns, lettered from K to W, have been identified from mutant strains of *S. spinosa*.

The term "spinosyn or a physiologically acceptable derivative or salt thereof" as used herein refers to an individual spinosyn factor (A, B, C, D, E, F, G, H, J, K, L, M, N, O, P, Q, R, S, T, U, V, W or Y), an N-demethyl derivative of an individual spinosyn factor, a combination thereof or a physiologically acceptable salt. For convenience, the term "spinosyn" will also be used herein to mean an individual spinosyn, or a physiologically acceptable derivative or salt thereof, or a combination thereof. Most preferred for wound healing in humans is spinosad or a physiologically acceptable derivative or salt thereof.

EP 375 316 describes spinosyns A-H and J (which they called A83543 factors A, B, C, D, E, F, G, H and J), and salts thereof. Mynderse, et al. described spinosyns L-N (which they called A83543 factors L, M and N), their N-demethyl derivatives, and salts thereof, in U.S. Pat. No. 5,202,242; and Turner, et al. described spinosyns Q-T (which they called A83543 factors Q, R, S and T), their N-demethyl derivatives, and salts thereof, in U.S. Pat. No. 5,591,606; and U.S. Pat. No. 5,631,155. These patents are incorporated herein by reference. Spinosyns K, O, P, U, V, W and Y are described, for example by Carl V. DeAmicis, James E. Dripps, Chris J. Hatton and Laura I. Karr in American Chemical Society's Symposium Series: Phytochemicals for Pest Control, Chapter 11, "Physical and Biological Properties of Spinosyns: Novel Macrolide Pest-Control Agents from Fermentation," pages 146-154 (1997). In U.S. Pat. No. 6,001,981, various synthetic derivatives of spinosyns are described, and U.S. Pat. No. 6,455,504, wherein various spinosyn analogs are described, which are both incorporated by reference herein. Details regarding the fermentation and isolation of the spinosyns and procedures for preparing synthetic derivatives are provided in these references.

Each of the U.S. Patent and EP patent application describe various formulation types, parasiticidal activity and administration options in animals and agriculture for the spinosyns and physiologically acceptable derivatives or salts thereof.

In U.S. Pat. Nos. 6,063,771 and 6,342,482, and in EP 1 252 820, formulations and use of spinosyns or a physiologically acceptable derivative or salt thereof for controlling lice on humans are described and processes for preparing these formulations.

As stated above, spinosad formulations are commercially available from Dow AgroSciences, 9330 Zionsville Road, Indianapolis, Ind., 46268-1054, U.S.A., and Elanco Animal Health, a Division of Eli Lilly and Company, P.O. Box 708, 2001 W. Main Street, Greenfield, Ind., 46140, U.S.A. In addition, *S. spinosa* and mutant strains have been deposited in the Agricultural Research Service Patent Culture Collection (NRRL) National Center for Agricultural Utilization Research, ARS, USDA, 1815 North University Street, Peoria, Ill., 61604, U.S.A. (NRRL 18395, 18537, 18538, 18539, 18719, 18720, 18743, 18823 and 30141 (U.S. Pat. No. 6,455,504).

The spinosyns can react to form salts. Salts that are physiologically acceptable are also useful in the methods of this invention. The salts are prepared using standard procedures for salt preparation. For example, spinosyn A can be neutralized with an appropriate acid to form an acid additional salt. The acid addition salts of spinosyns are particularly useful. Representative suitable acid addition salts include salts formed by reaction with either an organic or inorganic acid such as, for example, sulfuric, hydrochloric, phosphoric, acetic, succinic, citric, lactic, maleic, fumaric, cholic, pamoic, mucic, glutamic, camphoric, glutaric, glycolic, phthalic, tartaric, formic, lauric, stearic, salicylic, methanesulfonic, benzenesulfonic, sorbic, picric, benzoic, cinnamic and like acids.

All ratios, percentages, and parts discussed herein are "by weight" unless otherwise specified.

"Wound" means an injury to a human in which tissue is cut, torn, broken, burned, or otherwise traumatized, or results from a disorder or disease which results in such injury.

The "healing" which is afforded by the present invention is a promotion or acceleration of the time from when the wound occurs (a spinosyn is administered) until wound closure (full wound contraction).

The term "tissue" refers to a mass of cells in the human body which group together to form a specific function. Tissue includes, but is not limited to, bone, skin, connective, and nerve such as the spinal cord.

The terms "treating," "treatment" and "therapy" as used herein refer to curative therapy. Those in need of treatment include those humans having the wound, disorder or disease.

Administration "in combination with" one or more farther therapeutic agents includes simultaneous (concurrent) and consecutive administration in any order to humans.

A "therapeutically-effective amount" is the minimal amount of active agent (e.g., a spinosyn and most preferably spinosad) which is necessary to impart therapeutic benefit to a human. For example, a "therapeutically-effective amount" to a human suffering from a wound is such an amount which induces, promotes, accelerates or otherwise causes an improvement in the pathological symptoms, healing progression, physiological conditions associated with or ameliorates resistance to healing.

"Carriers" as used herein include pharmaceutically-acceptable carriers, excipients, or stabilizers which are nontoxic to the human being exposed thereto at the dosages and concentrations employed. Often the physiologically-acceptable carrier is an aqueous pH buffered solution. Examples of physiologically-acceptable carriers include buffers such as phosphate, citrate, and other organic acids; antioxidants including ascorbic acid; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as polyoxyethylene sorbitan fatty acid esters (TWEEN®), polyethylene glycol (PEG), and polyoxyethylene/polyoxypropylene blockcopolymers (PLURONIC®).

The spinosyns of the present invention and most particularly spinosad stimulate neurogenic activation of healing, and subsequent inflammatory activity involved in cell growth and proliferation. Accordingly, compositions of the present invention can be employed to stimulate epithelial cell proliferation and basal keratinocytes for the purpose of wound healing, particularly dermal wounds. These wounds may be of superficial nature or may be deep and involve damage of the dermis and the epidermis of skin.

Spinosyns are useful for treating a number of wounds and conditions. For example, spinosyns are active in vivo in various wound healing models.

The human to which spinosyns are administered may heal wounds at a normal rate or may be healing impaired. When administered to an individual who is not healing impaired, spinosyns are administered to accelerate the normal healing process. When administered to an individual who is healing impaired, spinosyns are administered to facilitate the healing of wounds which would otherwise heal slowly or not at all. A number of afflictions and conditions can result in healing impairment. These afflictions and conditions include diabetes (e.g., Type II diabetes mellitus), treatment with both steroids and non-steroid pharmacological agents, and ischemic blockage or injury.

A number of growth factors have been shown to promote wound healing in healing impaired individuals. These growth factors include growth hormone-releasing factor, platelet-derived growth factor, and basic fibroblast growth factors. Thus, the present invention also encompasses the administration of at least one spinosyn in conjunction with one or more growth factors or other agent which promotes wound healing.

The spinosyns of the present invention promote the healing of anastomotic and other wounds caused by surgical procedures in humans that heal wounds at a normal rate or are healing impaired.

The spinosyns of the present invention and particularly spinosad are clinically useful in stimulating wound healing of wounds including surgical wounds, excisional wounds, deep wounds involving damage of the dermis and epidermis, soft tissue injuries such as muscle tears, eye tissue wounds, dental tissue wounds, oral cavity wounds, wounds and ulcers of the gastro-intestinal mucosa, diabetic ulcers, dermal ulcers, cubitus ulcers, arterial ulcers, venous stasis ulcers, and burns resulting from heat, exposure to extreme temperatures of heat or cold, or exposure to chemicals, in normal individuals and those subject to conditions which induce abnormal wound healing such as uremia, malnutrition, vitamin deficiencies, obesity, infection, immunosuppression and complications associated with systemic treatment with steroids, radiation therapy, and antineoplastic drugs and antimetabolites. The compositions are also useful for promoting the healing of wounds associated with ischemia and ischemic injury, e.g., chronic venous leg ulcers caused by an impairment of venous circulatory system return and/or insufficiency; for promoting dermal reestablishment subsequent to dermal loss; increasing the tensile strength of epidermis and epidermal thickness; and increasing the adherence of skin grafts to a wound bed and to stimulate re-epithelialization from the wound bed.

As used herein, by "individual" is intended a human.

The spinosyn formulations may employ suitable pharmaceutical diluents that are known to be useful in pharmaceutical compositions. Such a diluents include but are not limited to, saline, buffered saline, dextrose, water, glycerol, ethanol, and combinations thereof. The formulation should suit the mode of administration. Preferably, the pharmaceutical compositions will be formulated for administration.

The spinosyn may be administered in pharmaceutical compositions in combination with one or more pharmaceutically acceptable excipients. It will be understood that, when administered to a human patient, the total daily usage of the pharmaceutical compositions of the present invention will be decided by the attending physician within the scope of sound medical judgment. The specific therapeutically effective dose level for any particular patient will depend upon a variety of factors including the type and degree of the response to be achieved; the specific composition, including whether another agent, if any, is employed; the age, body weight, general health, sex and diet of the patient; the time of administration, route of administration, and rate of excretion of the composition; the duration of the treatment; drugs (such as a chemotherapeutic agent) used in combination or coincidental with the specific composition; and like factors well known in the medical arts. Suitable formulations, known in the art, can be found in *Remington's Pharmaceutical Sciences* (latest edition), Mach Publishing Company, Easton, Pa. The "effective amount" of spinosyns for purposes herein (including a spinosyn effective amount) is thus determined by such considerations.

The pharmaceutical compositions of the present invention may be administered in a convenient manner such as by the oral, rectal, topical, intravenous, intraperitoneal, intramuscular, intraarticular, subcutaneous, intranasal, inhalation, intraocular or intradermal routes. Parenteral and topical delivery are the preferred routes of administration.

The term "parenteral" as used herein refers to modes of administration which include intravenous, intramuscular, intraperitoneal, intrasternal, subcutaneous and intraarticular injection and infusion.

The pharmaceutical compositions are administered in an amount which is effective for treating the specific indication. In most cases, the spinosyn dosage is from about 0.5 µg/kg to about 50 mg/kg body weight daily, taking into account the routes of administration, symptoms, etc. However, the dosage can be as low as 0.05 µg/kg body weight. For example, in the specific case of topical administration dosages are preferably administered from about 0.2 µg to 2 µg per $cm^2$. In the case of intranasal and intraocular administration, dosages are preferably administered from about 0.05 µg/kg to about 50 µg/kg body weight, and more preferably from about 0.5 µg/kg to about 5 µg/kg bodyweight.

As a general proposition, the total pharmaceutically effective amount of the spinosyn administered parenterally will be in the range of about 0.5 µg/kg/day to 5 mg/kg/day of patient body weight, although, as noted above, this will be subject to therapeutic discretion. If given continuously, the spinosyn is typically administered at a dose rate of about 10 µg/kg/hour to about 100 µg/kg/hour, either by 1-4 injections per day or by continuous subcutaneous infusions, for example, using a mini-pump. An intravenous bag solution or bottle solution may also be employed.

A course of spinosyn treatment appears to be optimal if continued longer than a certain minimum number of days, 1 to 5 days for humans. The length of treatment needed to observe changes and the interval following treatment for responses to occur will vary depending on the desired effect.

For parenteral administration, in one embodiment, the spinosyn if formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation.

Generally, the formulations are prepared by contacting the spinosyn uniformly and intimately with liquid carriers or finely divided solid carriers or both. Then, if necessary, the product is shaped into the desired formulation. In the case of a parenteral carrier, preferably a solution that is isotonic with the blood of the recipient is employed. Examples of such carrier vehicles include water, saline, Ringer's solution, and dextrose solution. Non-aqueous vehicles such as fixed oils and ethyl oleate are also useful herein, as well as liposomes. Suitable formulations, known in the art, can be found in *Remington's Pharmaceutical Sciences* (latest edition), Mach Publishing Company, Easton, Pa.

For topical administration, formulations such as ointments, creams, and gels may be used at the dosages described above for compositions. Suitable formulations, known in the art, can be found in *Remington's Pharmaceutical Sciences* (latest edition), Mach Publishing Company, Easton, Pa.

Ointments generally are prepared using either (1) an oleaginous base, i.e., one consisting of fixed oils or hydrocarbons, such as white petrolatum or mineral oil, or (2) an absorbent base, i.e. one consisting of any anhydrous substance or substances which can absorb water, for example, anhydrous lanolin. Customarily, following formation of the base, whether oleaginous or absorbent, the active ingredient (spinosyns) are added in an amount affording the desired concentration.

Creams are oil/water emulsions. They consist of an oil phase (internal phase), comprising typically fixed oils, hydrocarbons, and the like, such as waxes, petrolatum, mineral oil, and the like, and an aqueous phase (continuous phase), comprising water and any water-soluble substances, such as added salts. The two phases are stabilized by use of an emulsifying agent, for example, a surface active agent, such as sodium lauryl sulfate; hydrophilic colloids, such as acacia colloidal clays, veegum, and the like. Upon formation of the emulsion, the active ingredient (spinosyns) customarily are added in an amount to achieve the desired concentration.

Gels comprise a base selected from an oleaginous base, water, or an emulsion-suspension base, such as aforedescribed. To the base is added a gelling agent which forms a matrix in the base, increasing its viscosity. Examples of gelling agents are hydroxypropyl cellulose, acrylic acid polymers, and the like. Customarily, the active ingredient (spinosyns) are added to the formulation at the desired concentration at a point preceding addition of the gelling agent.

The oral pharmaceutical formulations are prepared by known procedures using well known and readily available ingredients. In making the compositions, the active ingredient will usually be admixed with a pharmaceutically acceptable carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, suspensions, emulsions, solutions, syrups, soft and hard gelatin capsules, and the like.

In addition to the active or therapeutic ingredient, at the dosages described above for compositions, tablets contain a number of inert materials known as additives or excipients. These materials help to impart satisfactory processing and compression characteristics to the formulation including diluents, binders, glidants and lubricants. A further group of added substances helps to give additional desirable physical characteristics to the finished tablet. Included in this group are disintegrants, colors, and in the case of chewable tablets, flavors and sweetening agents, and in the case of controlled-release tablets, polymers or waxes or other solubility-retarding materials.

By "pharmaceutically acceptable" it is meant the carrier, diluent or excipient must be compatible with the other ingredients of the formulation and not deleterious to the recipient thereof.

Further details, including representative formulations, can be found in *Remington's Pharmaceutical Sciences* (latest edition) Mach Publishing Company, Easton, Pa.

The present compositions also contemplate wound care dressings or bandages comprising a therapeutically effective amount of a spinosyn or a physiologically acceptable derivative or salt thereof. The bandage or dressing for wound care comprises an outer fabric support, preferably an elastomeric fabric support; and an inner pad, wherein the inner pad includes an outer membrane surface, preferably fabricated from a film-forming material, and incorporating a therapeutically effective amount of a spinosyn or a physiologically acceptable derivative or salt thereof, preferably spinosad or a physiologically acceptable derivative or salt thereof, at the dosages described above for compositions in the matrix. The pad may be integral with or separate from the outer fabric support.

The spinosyn is ideally incorporated into the membrane matrix, but may also be incorporated into the material of the inner pad contained by the membrane.

The therapeutically active agent is held in the polymeric matrix so that migration is inhibited, and permitting the gradual release over time of spinosyn.

In another aspect, the wound dressing comprises an absorbent pad having a liquid pervious body-side liner, a separate outer cover sheet, optionally liquid impervious, and an absorbent body disposed between. The inner and/or absorbent body are fabricated from materials which incorporate a therapeutically effective amount of a spinosyn in the matrix or interstutual spaces to ensure that the spinosyn is in constant close proximity to the wound.

The inner surface or pad of the bandage is preferably fabricated from a natural or synthetic membrane or film-forming material of either organic or inorganic, animal or vegetable origin, or from plastics materials. For example, from gelatins or from vegetable gums, or from hydrophilic or hydrophobic film forming plastics materials such polyvinylchlorides polyacetates or polyamides which are cast or coated as a film or membrane in the usual way.

Suitable polymeric materials include but are not limited to silastic or other silicone-based material, polyethylene tecephtalate (PET), Dacron, knitted Dacron, velour Dacron, polyglacin, nylon, silk, polyethylene (PE), polyurethane, polyvinyl chlorides silastic elastomer, silicone, rubber, PMMA (poly-(methylmethacrylate)), latex, polypropylene (PP), polyolefin, cellulose, polyvinyl alcohol (PVA), poly (hydroxyethylmethacrylate (PHEMA), poly(glycolic acid), poly(acrylonitrile) (PAN), fluoroethylene-cohexa-fluorporpylene (FEP), Teflon (PTFE), copolymers thereof and mixtures thereof.

The simplest method of incorporating the therapeutically active compounds into the polymeric material is by direct compounding of the therapeutically active substance into the plastic resin before casting or the like.

The film or membrane is ideally fabricated from a hydrophobic polymer which is both liquid and gas permeable, but impervious to the passage of micro-organisms. The hydrophobicity of the film or membrane is a useful feature in that it reduces the tendency for the film or membrane to become attached to the wound site.

The amount of spinosyns incorporated into the formulation is not critical; the concentration should only be in a range sufficient to permit ready application of the formulation to the wound area in an amount which will deliver the desired amount of spinosyns.

The customary amount of formulation to be applied to a wound will depend upon wound size and concentration of spinosyns in the formulation. Generally, the formulation will be applied to the wound in an amount affording from about 0.1 µg to about 5 µg spinosyns per cm$^2$ of wound. Preferably, the applied amount of spinosyns will range from about 0.2 µg to about 2 µg/cm$^2$, and, most preferably, from about 0.25 µg to about 0.5 µg/cm$^2$.

Spinosyns may also be administered to the eye to treat lacrimal gland injuries, disorders and pathologies in humans as a liquid, drop, or thickened liquid, a gel.

Spinosyns can also be intranasally administered to the nasal mucosa to treat disorders, injuries and pathologies of the nasal mucosa and sinus epithelia in humans as liquid drops or in a spray form.

Spinosyns are typically formulated in vehicles at a concentration of about 0.01 μg/ml to 50 mg/ml, preferably 0.01 μg/ml to 10 mg/ml, at a pH of about 5 to about 8, preferably about 6 to about 7, most preferably about pH 6.2. It will be understood that the use of certain of the foregoing excipients, carriers, or stabilizers may result in the formation of spinosyn salts.

Spinosyns ordinarily will be stored in unit or multi-dose containers, for example, sealed ampules or vials, as an aqueous solution or as a lyophilized formulation for reconstitution. As an example of a lyophilized formulation, 3-ml vials are filled with 1 ml of sterile-filtered 1% (w/v) aqueous spinosyn solution, and the resulting mixture is lyophilized. The infusion solution is prepared by reconstituting the lyophilized spinosyn using Water-for-Injection which may optionally include one or more antioxidants.

Dosages may also be arranged in a patient specific manner to provide a predetermined concentration of a spinosyn activity in the blood, as determined by an RIA technique, for instance. Thus, patient dosaging may be adjusted to achieve regular on-going trough blood levels, as measured by RIA, on the order of from 50 to 1000 ng/ml, preferably 150 to 500 ng/ml.

EXAMPLE 1

Topical Application of Spinosad Improves the Healing of Wounds from Mulesing Operation in Sheep. (Study Number T9CAL0205)

Castrated and tail-docked Merino lambs are mulesed (mulesing involves surgical removal of wool-bearing skin from the crutch area, and when healed, reduces susceptibility of sheep to fly strike). Fifty sheep are left untreated and a group of 381 are treated with 7.1 g of 4 mg/g spinosad aerosol (refer to Table 1 for formulation). Spinosad aerosol is applied topically to the wound until wet with product, taking care to part the

TABLE 1

Spinosad aerosol formulation

| Component | Quantity % w/w |
| --- | --- |
| Spinosad @89.9% | 0.445 |
| Alcohol 100AGF4 | 20 |
| Chlorhexidine digluconate 20% | 0.08 |
| Brilliant blue FCF | 0.02 |
| Propyl gallate | 0.01 |
| Lactic acid 85% | 0.06 |
| Propylene glycol | 10 |
| Deionized water | 64.43 |
| Tween 20 | 2 |
| PVP K30 | 3 |

The mulesing wounds of 18 lambs per group are closely examined and assessed for evidence of wound healing at 7 and 17 days after treatment (Table 1). Scab formation and wound contraction are scored from 0 (complete or normal healing) to 3 (equivalent to no healing). Hemorrhage/serous effusion and impaired healing are visually scored from 0 (absence of hemorrhage/effusion and normal healing) to 3 (severe hemorrhage or impaired healing).

TABLE 2

The effect of topical spinosad application on wound healing in sheep after mulesing operation.

| | Group | | | | | | | |
| --- | --- | --- | --- | --- | --- | --- | --- | --- |
| | #Scab Formation | | #Wound Contraction | | #Hemorrhage/ Serous Effusion | | @Healing Impaired | |
| | Day | | | | | | | |
| | 7 | 17 | 7 | 17 | 7 | 17 | 7 | 17 |
| Untreated | 0.04 | 0.57 | 0.12 | 0.88 | 0.12 | 0.08 | 0 | 0 |
| Spinosad aerosol | 0.04 | 0 | 0.08 | 0.36 | 0.12 | 0 | 0 | 0 |

Geometric means. Low scores indicate better healing.
@Number of affected sheep out of 18.

At day 7 after mulesing, sheep treated with spinosad have greater contraction of mulesing wounds than untreated controls, as determined by lower mean scores for wound contraction. By 17 days after mulesing, sheep treated with spinosad have improved scab formation, wound contraction and reduced hemorrhage and serous effusion, indicating improved wound healing, compared with untreated control sheep.

Topical application of spinosad to the mulesing wounds of sheep will result in improved wound healing 17 days after treatment compared with untreated animals. This improvement in wound healing occurs in the absence of confounding factors such as blow fly strike. However, the formulation used in this example also included an antibacterial compound, chlorhexidine. The ability of chlorhexidine to inhibit bacterial infection may also be having a positive effect on wound healing in this example.

EXAMPLE 2

Topical Application of Spinosad Improves the Healing of Wounds from Mulesing Operation in Sheep. (Study Number T9CAL0206)

Tail-docked and crutched Merino ewe lambs are mulesed. Approximately 46 ml of diluted (125 ppm) Extinosad (refer to Table 3 for formulation) is applied to the mulesing wounds of 150 lambs using a small (2 or 5 L) pressurized garden hand spray applicator available at man retail stores having garden supplies. The container or reservoir is conical shaped and pressurized by manual pumping. The spray is delivered from a cone nozzle. Spinosad aerosol 4 mg/g (refer to Table 1 for formulation) is applied to the wound using an aerosol spray until the wound and surrounding wool is wet with product. Fifty sheep remain untreated after mulesing (control).

TABLE 3

Extinosad (25 g/L spinosad) formulation

| Component | Quantity % w/w |
| --- | --- |
| Spinosad @ 92% | 2.7 |
| Veegum | 1 |
| Proxel GXL | 0.2 |

TABLE 3-continued

Extinosad (25 g/L spinosad) formulation

| Component | Quantity % w/w |
|---|---|
| Propylene glycol | 10 |
| Xanthum gum | 0.2 |
| Pluronic P123 or Pluronic P105 | 1.0 |
| Antifoam C (30%) | 0.2 |
| Lomar PWA (44.5% solution) | 4.5 |
| Deionized water | 80.2 |

Fourteen days after treatment the lambs are mustered and held in pens. Over a period of 15 minutes the lambs are observed and any with signs of fly strike such as twitching of the tail, biting at the area or stamping of a foot are identified. Twenty-five lambs from each group are randomly selected and placed over a rail and their mulesing wounds assessed for evidence of fly strike and wound healing (Table 4). Scab formation and wound contraction are scored from 0 (complete or normal healing) to 3 (equivalent to no healing). Hemorrhage/serous effusion and impaired healing are visually scored from 0 (absence of hemorrhage/effusion and normal healing) to 3 (severe hemorrhage or impaired healing).

TABLE 4

The effect of topical spinosad application, delivered in 2 different formulations, on wound healing, and the presence of fly strike and infection in sheep 14 days after mulesing operation and treatment.

| Group | #Scab Formation | #Wound Contraction | #Hemorrhage/ Serous Effusion | @Healing Impaired | @Larvae Present | @Infection Present |
|---|---|---|---|---|---|---|
| Untreated | 0.15 | 0.15 | 0.15 | 4 | 4 | 6 |
| Extinosad (spinosad 125 mg/L) | 0.06 | 0.03 | 0 | 0 | 1 | 0 |
| Spinosad Aerosol (4 mg/L) | 0.03 | 0.06 | 0 | 0 | 0 | 0 |

Geometric means. Low scores indicate better healing.
@Number of affected sheep out of 25.

Sheep treated with spinosad, either as an aerosol formulation (4 mg/L) or as a manual spray (125 mg/L) show improved wound healing, as evidenced by a reduced scored for scab formation, wound contraction and the presence of hemorrhage and serous effusion at the wound site. Furthermore, of the 25 sheep examined in each treatment group, none of the animals are healing impaired, compared with 4 healing impaired animals noted in the untreated control group. Larvae from Lucilia cuprina are present in 4 out of 25 untreated control sheep, compared with one sheep from the group treated with Extinosad, and no sheep from the group treated with spinosad aerosol. Infection at the wound site is present in 6 out of 25 sheep in the untreated group, but absent in the groups treated with spinosad.

Topical treatment of mulesing wounds with spinosad results in improved wound healing compared with untreated control animals, as seen in Example 1 above. This improvement in wound healing is accompanied by reduced infection rates and reduced presence of Lucilia cuprina larvae. The improvement in wound healing occurs regardless of the formulation or dose of spinosad applied to the wounds at mulesing. Furthermore, spinosad, in the absence of chlorhexidine (Extinosad) is able to enhance wound healing. This data suggests the enhanced wound healing seen in Examples 1 and 2 may be the effect of spinosad itself, rather than the infection-inhibiting properties of chlorhexidine.

EXAMPLE 3

Spinosad Improves Wound Healing in Rats Using a Thermal Injury Model a) The Effect of Spinosad on the Healing of Laser-Induced Wounds in Normal, Young Rats.

Young outbred male Sprague-Dawley rats, 3 months of age and approximately 300 g have, the hair removed from the interscapular region 24 h prior to wound induction. Rats are anaesthetised and a thermal burn induced using a $CO_2$ laser (four consecutive stimulation periods each at 25 watts power, 0.5 sec pulse with the beam spot diameter set at 10 mm), resulting in a circular wound area of 2 $cm^2$. Groups of 12 rats are treated with saline, citric acid (5%) or spinosad (0.5% in 5% citric acid). Treatments are delivered twice daily for 5 days after wound induction, via 2 intradermal injections of 100 µl on opposing sides of the wound.

Scab formation causes a transient decrease in the rate of wound contraction (Snowden et al., *Aust. J. Exp. Biol. Med. Sci.* 60: 73-82 (1982)). Therefore, scab and lightly adherent eschar are gently removed upon detection, to keep all wounds comparable and permit accurate tracing of wound area.

Wounds are measured daily for 6 consecutive days after wound induction, and every 48 h thereafter until complete wound closure/re-epithelialisation has occurred. The area of burn (maximum diameter of the wound) was traced under a stereo microscope for accuracy and then measured with a digital planimeter. The healing endpoint is the time when full wound contraction has occurred (Table 5).

TABLE 5

Effect of spinosad (0.5%) on the rate of wound healing in rats exposed to thermal burn injury, compared with saline and citric acid controls.

| Days after initiation of wound | Size of wound, $cm^2$ (group mean ± SEM, n = 12) | | |
|---|---|---|---|
| | saline | Citric acid | Spinosad 0.5% |
| 1 | 2.5 ± 0 | 2.6 ± 0.1 | 2.6 ± 0.1 |
| 2 | 2.8 ± 0.1 | 3.1 ± 0.1 | 1.9 ± 0.1 |
| 3 | 4.1 ± 0.2 | 4.5 ± 0.2 | 1.7 ± 0.1 |

TABLE 5-continued

Effect of spinosad (0.5%) on the rate of wound healing in rats exposed to thermal burn injury, compared with saline and citric acid controls.

| Days after initiation of wound | Size of wound, cm² (group mean ± SEM, n = 12) | | |
| --- | --- | --- | --- |
| | saline | Citric acid | Spinosad 0.5% |
| 4 | 4.3 ± 0.1 | 4.4 ± 0.2 | 1.4 ± 0.1 |
| 5 | 4.5 ± 0.1 | 4.8 ± 0.1 | 1.3 ± 0.1 |
| 7 | 3.4 ± 0.1 | 3.6 ± 0.2 | 1.2 ± 0.1 |
| 9 | 2.3 ± 0.3 | 2.5 ± 0.1 | 1.0 ± 0.1 |
| 11 | 1.9 ± 0.1 | 1.5 ± 0.2 | 0.4 ± 0.1 |
| 12 | * | * | resolved |
| 13 | 1.1 ± 0.1 | 0.6 ± 0.2 | |
| 15 | 0.4 ± 0.2 | 0.1 ± 0 | |
| 16 | resolved | resolved | |

The effect of spinosad on wound healing is noticeable by day 2 after wound induction, whence spinosad treated rats had wounds 30% smaller than those of saline and citric acid treated controls. Rats treated with spinosad show complete resolution of the wound by day 12, which is 4 days earlier than their counterparts treated with saline or citric acid.

These data show that a simple, aqueous solution of spinosad can expedite the healing of wounds in normal, young healthy rats.

b) The Effect of Spinosad on the Healing of Laser-Induced Wounds in Diabetic (Healing Impaired) Rats Induction of Diabetes using Streptozotocin Diabetes is induced in 3 month old outbred male Sprague-Dawley rats using streptozotocin (STZ). Streptozotocin (75 mg/kg) is dissolved in 0.1M cold sodium citrate buffer (pH 4) and kept on ice to avoid decomposition. After 24 hrs of fasting, rats are injected intraperitoneally with a single dose of freshly prepared (cold) STZ (Rakienten et al., Cancer Chemotherapy Report 29: 73-82 (1963)). Symptoms of diabetes became apparent in these rats within 2-3 days and their diabetic condition is confirmed by urine glucose test. Insulin treatment is used to give regular respite from the catabolic dominance of the condition while allowing regular and severe hyperglycaemia (Willars et al., J. Neurol. Sci. 91: 153-164 (1989)). One to two injections of insulin (Protophane 2 IU/100 g) are given subcutaneously to the newly diabetic rats depending on the severity of their physical condition (e.g. little eating or drinking, weight loss to around 115 g, extreme inactivity). Rats that failed to improve or lost more than 15% of their body weight are sacrificed.

Diabetic rats of approximately 200 g had the hair removed from the interscapular region 24 h prior to wound induction. Rats are anaesthetised and a thermal burn induced using a $CO_2$ laser (four consecutive stimulation periods each at 25 watts power, 0.5 sec pulse with the beam spot diameter set at 10 mm), resulting in a circular wound area of 2 cm². Groups of 12 rats are treated with either saline or spinosad (0.5% in 5% citric acid). Treatments are delivered topically twice daily for 5 days after wound induction, by dropping 100 µl of solution directly onto the wound site.

Scab and lightly adherent eschar are gently removed upon detection, to keep all wounds comparable and permit accurate tracing of wound area. Wounds are measured as described above (Example 3a), until wound closure is apparent (Table 6).

TABLE 6

Effect of spinosad (0.5%) on the rate of wound healing in diabetic rats exposed to thermal burn injury, compared with saline controls.

| Days after initiation of wound | Size of wound, cm² (group mean, n = 12) | |
| --- | --- | --- |
| | saline | Spinosad 0.5% |
| 1 | 2.2 ± 0 | 2.1 ± 0 |
| 2 | 2.2 ± 0.1 | 2.1 ± 0.1 |
| 3 | 2.1 ± 0.1 | 1.5 ± 0.1 |
| 4 | 2.1 ± 0.1 | 1.6 ± 0.1 |
| 5 | 2.4 ± 0.2 | 1.9 ± 0.1 |
| 6 | 3 ± 0 | 2.5 ± 0.2 |
| 8 | 3 ± 0.1 | 2.1 ± 0.1 |
| 10 | 2.3 ± 0.2 | 1.2 ± 0.2 |
| 12 | 1.2 ± 0.1 | 0.6 ± 0.1 |
| 13 | * | resolved |
| 14 | 0.6 ± 0.1 | |
| 16 | 0.2 ± 0.1 | |
| 17 | resolved | |

Diabetic rats topically with spinosad show improved wound healing compared with saline controls 3 days after wound induction, as illustrated by reduced wound area. Wound size continues to contract more quickly in spinosad-treated rats, resulting in would resolution at day 13, 4 days earlier than wound resolution occurs in saline-treated controls.

c) The Effect of Spinosad on the Healing of Laser-Induced Wounds in Aged (Healing Impaired) Rats Outbred male Sprague-Dawley rats, 24 months of age and approximately 600 g had the hair removed from the interscapular region 24 h prior to wound induction. Rats are anaesthetised and a thermal burn induced using a $CO_2$ laser (four consecutive stimulation periods each at 25 watts power, 0.5 sec pulse with the beam spot diameter set at 10 mm), resulting in a circular wound area of 2 cm². Groups of 12 rats are treated with either saline or spinosad (0.5% in 5% citric acid). Treatments are delivered topically twice daily for 5 days after wound induction, by dropping 100 µl of solution directly onto the would site.

Scab and lightly adherent eschar are gently removed upon detection, to keep all wounds comparable and permit accurate tracing of wound area. Wounds are measured as described above (Example 3a), until wound closure is apparent (Table 7).

TABLE 7

Effect of spinosad (0.5%) on the rate of wound healing in aged rats exposed to thermal burn injury, compared with saline controls.

| Days after initiation of wound | Size of wound, cm² (group mean, n = 12) | |
| --- | --- | --- |
| | saline | Spinosad 0.5% |
| 1 | 2.3 ± 0 | 2.4 ± 0 |
| 2 | 2.3 ± 0 | 2.9 ± 0.1 |
| 3 | 3.5 ± 0.2 | 2.7 ± 0.2 |
| 4 | 4 ± 0.2 | 2.3 ± 0.2 |
| 5 | 4.9 ± 0.2 | 2 ± 0.2 |
| 6 | 5.6 ± 0.2 | 3.3 ± 0.1 |
| 8 | 4.6 ± 0.1 | 3.5 ± 0.1 |
| 10 | 3.2 ± 0.1 | 2.5 ± 0.2 |
| 12 | 2.2 ± 0.1 | 1.2 ± 0.1 |
| 14 | 1.6 ± 0.1 | 0.8 ± 0.1 |
| 15 | * | resolved |
| 16 | 1.2 ± 0 | |

TABLE 7-continued

Effect of spinosad (0.5%) on the rate of wound healing in aged rats exposed to thermal burn injury, compared with saline controls.

| Days after initiation of wound | Size of wound, cm² (group mean, n = 12) | |
|---|---|---|
| | saline | Spinosad 0.5% |
| 18 | 0.9 ± 0.1 | |
| 20 | 0.5 ± 0.1 | |
| 21 | resolved | |

Aged rats treated topically with spinosad show improved wound healing compared with saline controls 3 days after wound induction, as illustrated by reduced wound area. Wound size continues to contract in spinosad-treated rats, up to day 6, during which time wound size is increasing in saline-treated rats. Rats treated with spinosad continue to have reduced wound size compared with saline controls, resulting in wound resolution at day 15, 6 days earlier than wound resolution occurs in saline-treated controls.

Spinosad improves the rate of wound healing whether applied topically or intradermally.

Spinosad improves wound healing in aged rats, which have chronic sensory nerve deficiencies. Such data suggests that spinosad may be enhancing wound healing via a sensory nerve dependent and sensory nerve independent mechanisms. Spinosad may therefore heal chronic ulceration associated with ageing.

Spinosad improves wound healing in rats with induced diabetes, another form of sensory nerve deficiency. This data also suggests that the wound-healing properties of spinosad may be modulated via both sensory nerve dependent and independent pathways. Spinosad may therefore heal chronic ulcerations and other wounds associated with poor healing in diabetics.

Spinosad improves healing in normal, young healthy rats with intact sensory nerves. Such findings suggest that spinosad may either be operating through a sensory nerve independent mechanism, or may be enhancing the functioning of sensory nerves. Spinosad may therefore enhance wounds in healthy human patients, such as those that occur with injury or surgery.

The results from Example 3 indicate that spinosad may stimulate wound healing via a number of mechanisms, and would be effective in both healing impaired and normal humans.

Diabetic and aged rats generally show a lag period prior to any significant response to injury (Tables 6 & 7) compared with healthy young rats (Table 5). This lag period has been attributed to a general decline in the activity of afferent sensory neurons of diabetic (Gibran et al., *J. Surg. Res.* 108: 122:128 (2002)) and aged (Khalil & Helme, *J. Gerontol. Biol. Sci.* 51A(5): B354-B361 (1996)) rats, evident during the inflammatory phase of wound healing. That spinosad is able to generate a wound healing effect in diabetic rats may be due to stimulation of local afferent sensory nerves or the use of mechanisms independent of afferent sensory nerve activation independent mechanisms.

The effect of spinosad is more pronounced in control animals with intact sensory nerves (Table 5). This effect is particularly obvious during the early inflammatory phase (days 2-5), the early component of the proliferative phase (days 2-6), with further positive effect during the late component of the proliferative phase (days 6-8) and the remodelling phase (days 9-12).

Spinosad also appears to have effect during the remodelling phase of wound repair, which involves cellular infiltration and proliferation. The dermis responds to injury during this phase by producing collagen and matrix proteins which result in wound contraction and resolution. Spinosad may therefore be having an effect on mediators influencing cellular infiltration and activation, such as cytokines, chemokines and other cell signallers, or may directly enhance the production of matrix and the remodelling of skin at the wound site.

Example 3 shows that spinosad improves the healing of wounds throughout the 3 phases of healing. The data from Example 3 confirm the results from Examples 1 and 2, that spinosad assists the healing of wounds, induced either surgically or by burning. Spinosad enhanced wound healing in 2 species.

EXAMPLE 4

Investigations into the Mode of Action of Spinosad in Enhancing Wound Healing in Rats Using a Blister Model of Neurogenic Inflammation a) Effect of Spinosad Dose on Vascular Flow Neurogenic inflammatory responses are assessed using a well-established method (Khalil & Helme, *Brain Res.* 527: 292-298 (1990)). Anaesthesia is induced in outbred male Sprague-Dawley rats with pentobarbitone sodium (60 mg/kg i.p). General anaesthesia is maintained by supplementary injections of 15 mg/kg. This method of anaesthesia has been shown not to alter the basal vasodilator responses in peripheral microvasculature (Khalil & Helme, *Brain Res.* 500: 256-262 (1989)). The left jugular vein is cannulated with polyethylene tubing for the intravenous administration of heparin/saline solution or drugs. Body temperature is maintained at 37° C. At the completion of the experiment, the animals are sacrificed by barbiturate overdose.

Blisters are induced in the middle region of the hindpaw in anaesthetised rats using vacuum pressure of −40 kPa applied for 30 minutes via a metal suction cap heated to 40° C. Once a blister is established, the epidermis (surface epithelium) is removed and a perspex chamber with inlet and outlet ports secured over the blister base. Ringer's solution is perfused over the blister surface and maintained by a peristaltic pump at 4 ml/hr to establish baseline measurements. Relative blood flow is monitored over time by a laser Doppler flowmeter via a probe placed immediately above the blister base and relative blood flux (volts) monitored continuously on a chart recorder.

Spinosad is diluted in 5% citric acid in Ringer's solution and perfused over the blister base for up to 30 minutes.

TABLE 8

The effect of different concentrations of spinosad on blood flow over the blister base, compared with Ringer's solution.

| | Concentration of spinosad | | |
|---|---|---|---|
| | 0.05% | 0.5% | 5% |
| Area under the curve cm² (mean ± SEM, n = 6) | 32 (±5) | 113.6 (±9.4) | 62.4 (±4.8) |

Spinosad perfused across the blister wound at a concentration of 0.5% has the greatest effect on vascular flow, in terms of both the height of the response and the duration of response. A solution of 0.05% spinosad has a positive effect on blood flow, although the magnitude of response is reduced compared with 0.5% spinosad. Spinosad at a concentration of 5% produces an intermediate response with a peak of reduced duration and magnitude compared to the response obtained with 0.5% spinosad. The maintained magnitude of response seen with 0.5% spinosad is suggestive of interaction with calcitonin gene related peptide (CGRP) nerve pathways, while the desensitization seen with the higher concentration of spinosad is often associated with substance P mediated pathways. These data show that spinosad has a positive effect on vascular flow, an essential requirement for wound healing. This action may be due to direct action on blood vessels or via the release of peptides such as CGRP and substance P from sensory nerves which in turn mediate a vascular response.

b) Effect of Sensory Nerve Peptide Antagonists and Nitric Oxide Synthase Inhibitor on the Vascular Response of Rats to 0.5% Spinosad Neurogenic inflammatory responses are assessed using a well-established method (Khalil & Helme, *Brain Res.* 527: 292-298 (1990)). Anaesthesia is induced in outbred male Sprague-Dawley rats with pentobarbitone sodium (60 mg/kg i.p). General anaesthesia is maintained by supplementary injections of 15 mg/kg. This method of anaesthesia has been shown not to alter the basal vasodilator responses in peripheral microvasculature (Khalil & Helme, *Brain Res.* 500: 256-262 (1989)). The left jugular vein is cannulated with polyethylene tubing for the intravenous administration of heparin/saline solution or drugs. Body temperature is maintained at 37° C. At the completion of the experiment, the animals are sacrificed by barbiturate overdose.

Blisters are induced in the middle region of the hindpaw in anaesthetised rats using vacuum pressure of −40 kPa applied for 30 minutes via a metal suction cap heated to 40° C. Once a blister is established, the epidermis (surface epithelium) is removed and a perspex chamber with inlet and outlet ports secured over the blister base. Ringer's solution is perfused over the blister surface and maintained by a peristaltic pump at 4 ml/hr to establish baseline measurements. Relative blood flow is monitored over time by a laser Doppler flowmeter via a probe placed immediately above the blister base and relative blood flux (volts) monitored continuously on a chart recorder.

Spinosad is diluted in 5% citric acid in Ringer's solution and perfused over the blister base for up to 30 minutes. One footpad of each rat is perfused with 0.5% spinosad, while the other footpad of each rat is first perfused with an antagonist or inhibitor for 10 minutes followed by co-perfusion with 0.5% spinosad for 30 minutes. $CGRP_{8-37}$ (CGRP antagonist; Auspep, VIC, Australia) is perfused at 1 μM, N-nitro L-arginine methyl ester (L-NAME, an endothelial nitric oxide synthase inhibitor; Cayman Chemical Co., MI, USA) is perfused at 100 μM, and spantide II (substance P antagonist II; Auspep, VIC, Australia) is perfused at 10 μM.

TABLE 9

The effect of sensory nerve peptide antagonists and eNOS inhibitor on the vascular response of rat footpad blisters to perfusion with 0.5% spinosad, and the relative contribution of effectors to the activity of spinosad.

| Substance perfused | Effector | Blood flow as area under the curve ($cm^2$) mean ± SEM, n = 6 | % contribution of effector to the vascular response of spinosad |
|---|---|---|---|
| Control | Nil | 113.6 (±9.4) | 100 |
| L-NAME | eNOS | 87.2 (±5.2) | 24 |
| $CGRP_{8-37}$ | CGRP | 83.2 (±6.5) | 27 |
| Spantide | Substance P | 74.9 (±3.6) | 34 |

Blood flow in response to spinosad stimulation is decreased in the presence of CGRP and SP peptide antagonists and a NOS inhibitor (Table 9). These data indicate that the effect of spinosad on vascular blood flow is mediated through CGRP, substance P and nitric oxide pathways. The contribution of CGRP, substance P and eNO to the effect of spinosad is 27%, 34% and 24% respectively (Table 9).

The vascular response profile in the presence of a CGRP antagonist has a similar magnitude of response throughout perfusion, suggesting that the mediation of the effect of spinosad by CGRP is constant over time. The vascular response profiles in the presence of the substance P antagonist (spantide) or the eNOS inhibitor (L-NAME) show that the response decreases over time. This suggests that substance P and eNOS have greater involvement in the mediation of the effect of spinosad during the later stages of the response.

These data collectively show that the effect of spinosad on vascular flow is mediated through the sensory nerve peptides substance P and CGRP, and through endothelial nitric oxide. The involvement of eNO in this process suggests that spinosad may act directly on the endothelium of blood vessels, as well as through sensory nerve innervation of blood vessels in wounds. Furthermore, the effect of spinosad is of long duration and mediated through different effectors at different stages of the response. Such findings may explain the differences in wound healing profiles between spinosad treated rats and control rats in the thermal injury model (Example 3), particularly the early resolution of wounds in healing-impaired (aged or diabetic) rats. The ability of neuropeptide inhibitors and antagonists to inhibit the action of spinosad on vascular flow suggests that the early wound healing property of spinosad is acting through sensory nerve pathways, and involves a combination of neuropeptides. Such activity would enhance the early inflammatory stage of the wound-healing process which is largely initiated by sensory nerve activity (Steinhoff et al., *Arch. Dermatol.* 139: 1479-1488 (2003)). Indeed, data from Example 3 show that in normal young rats and healing-impaired rats, the effect of spinosad on the contraction of wounds is pronounced during the first 5 days of healing.

c) The Effect of Spinosad on Vascular Response During the Early and Late Phases of Acute Inflammation.

Neurogenic inflammatory responses are assessed using a well-established method (Khalil & Helme, *Brain Res.* 527: 292-298 (1990)). Anaesthesia is induced in outbred male Sprague-Dawley rats with pentobarbitone sodium (60 mg/kg i.p). General anaesthesia is maintained by supplementary injections of 15 mg/kg. This method of anaesthesia has been shown not to alter the basal vasodilator responses in peripheral microvasculature (Khalil & Helme, *Brain Res.* 500: 256-262 (1989)). The left jugular vein is cannulated with polyethylene tubing for the intravenous administration of heparin/saline solution or drugs. Body temperature is maintained at 37° C. At the completion of the experiment, the animals are sacrificed by barbiturate overdose.

Blisters are induced in the middle region of the hindpaw in anaesthetised rats using vacuum pressure of −40 kPa applied for 30 minutes via a metal suction cap heated to 40° C. Once a blister is established, the epidermis (surface epithelium) is removed and a perspex chamber with inlet and outlet ports secured over the blister base. Ringer's solution is perfused over the blister surface and maintained by a peristaltic pump at 4 ml/hr to establish baseline measurements. Relative blood flow is monitored over time by a laser Doppler flowmeter via a probe placed immediately above the blister base and relative blood flux (volts) monitored continuously on a chart recorder.

Spinosad (0.5%) is diluted in 5% citric acid in Ringer's solution and perfused over the blister base for up to 30 minutes. The blister on one footpad of each rat is perfused immediately with spinosad (early phase), while the blister on the other footpad is perfused 5 hours after blister induction (late phase)

TABLE 10

The effect of spinosad 0.5% on the vascular response of footpad blisters during the early (immediately after injury) and late (5 h post-injury) phases of acute inflammation.

| | Phase of inflammation | |
|---|---|---|
| | Early phase | Late phase |
| Area under the curve (cm$^2$) Mean ± SEM, n = 6 | 113.6 (±9.4) | 95.5 (±9.3) |

Neurogenic effectors are predominantly involved in the early phase of the inflammatory response, while the late phase of the inflammatory response involves components of the immune system such as neutrophils and monocytes. That spinosad has almost equal effect in the early and late phases of the inflammatory response (Table 10) suggests that spinosad not only acts on neurogenic mediators of inflammation (also shown in Example 4b), but also has a significant effect on immunological mediators of the inflammatory response. This result is significant due to the involvement of immune mediators in the recruitment and activation of cells during the proliferative and remodelling phases of wound healing (days 6-12). As previously noted in Example 3, the effect of spinosad on wound healing is seen in the inflammatory, proliferative and remodelling phases. The data from the current example provide evidence that spinosad is stimulating both neurogenic and immunologic pathways to mediate its wound healing effects.

We claim:

1. A method of directly promoting or accelerating wound healing in a mammal comprising administering to a mammal having a wound a therapeutically effective amount of a spinosyn or a physiologically acceptable derivative or salt thereof in order to directly promote or accelerate the wound healing process in the mammal.

2. The method of claim 1 wherein said mammal is not healing impaired.

3. The method of claim 1 wherein said mammal is healing impaired.

4. The method of claim 1 wherein said spinosyn is topically applied to said wound.

5. The method of claim 1 wherein said spinosyn is orally administered.

6. The method of claim 1 wherein said spinosyn is parenterally administered.

7. The method of claim 1 wherein said mammal is a human.

8. The method of claim 1 wherein said mammal is a sheep.

9. The method of claim 1 wherein said spinosyn is spinosad or a physiologically acceptable salt thereof.

10. The method of claim 9 wherein said mammal is a human.

11. The method of claim 10 wherein said human is healing impaired.

12. The method of claim 10 wherein said spinosyn is topically or orally administered.

13. The method of claim 10 wherein said spinosyn is parenterally administered.

14. The method of claim 9 wherein said administration directly stimulates both neurogenic and immunological pathways to mediate wound healing.

* * * * *